(12) United States Patent
Rosendahl et al.

(10) Patent No.: US 8,629,079 B2
(45) Date of Patent: Jan. 14, 2014

(54) PROCESS FOR PRODUCING A CATALYST FOR THE OXIDATION OF ETHYLENE TO ETHYLENE OXIDE

(75) Inventors: Tobias Rosendahl, Mannheim (DE); Torsten Mäurer, Lambsheim (DE); Cornelia Katharina Dobner, Ludwigshafen (DE); Thomas Geiger, Römerberg (DE); Achim Gritsch, Rotterdam (NL)

(73) Assignee: BASF SE (DE)

( * ) Notice: Subject to any disclaimer, the term of this patent is extended or adjusted under 35 U.S.C. 154(b) by 0 days.

(21) Appl. No.: 13/446,379

(22) Filed: Apr. 13, 2012

(65) Prior Publication Data

US 2012/0264951 A1 Oct. 18, 2012

Related U.S. Application Data

(60) Provisional application No. 61/475,244, filed on Apr. 14, 2011.

(51) Int. Cl.
*B01J 23/48* (2006.01)

(52) U.S. Cl.
USPC .......................................................... 502/347

(58) Field of Classification Search
USPC .......................................................... 502/347
See application file for complete search history.

(56) References Cited

U.S. PATENT DOCUMENTS

| | | | |
|---|---|---|---|
| 5,070,058 A | 12/1991 | Sawicki et al. | |
| 5,102,848 A * | 4/1992 | Soo et al. | 502/218 |
| 5,525,740 A | 6/1996 | Rizkalla | |
| 2008/0015393 A1* | 1/2008 | Matusz et al. | 568/497 |
| 2008/0039316 A1 | 2/2008 | Bhise et al. | |
| 2008/0081920 A1* | 4/2008 | Gueckel | 549/533 |

FOREIGN PATENT DOCUMENTS

| | | |
|---|---|---|
| DE | 23 00 512 A1 | 7/1973 |
| DE | 24 54 972 A1 | 6/1975 |
| DE | 25 21 906 A1 | 12/1975 |
| EP | 14 457 A2 | 8/1980 |
| EP | 0082609 A1 | 6/1983 |
| EP | 0085237 A1 | 8/1983 |
| EP | 0172565 A2 | 2/1986 |
| EP | 0266015 A1 | 5/1988 |
| EP | 0339748 A2 | 11/1989 |
| EP | 0357293 A1 | 3/1990 |
| EP | 384 312 A1 | 8/1990 |
| EP | 0764464 A2 | 3/1997 |
| EP | 0804289 A1 | 11/1997 |
| EP | 0923986 A1 | 6/1999 |
| EP | 1002575 A2 * | 5/2000 |
| EP | 1086743 A1 | 3/2001 |
| EP | 1210301 A1 | 6/2002 |
| WO | WO-200183105 A1 | 11/2001 |
| WO | WO-03086624 A1 | 10/2003 |
| WO | WO-2004094054 A2 | 11/2004 |
| WO | WO-2007081379 A2 | 7/2007 |
| WO | WO-2007123932 A2 | 11/2007 |
| WO | WO-2009042300 A1 | 4/2009 |

OTHER PUBLICATIONS

Ulmann's Encyclopedia of Industrial Chemistry, 5th edition, vol. A-10, pp. 117-135, 123-125, VCH-Verlagsgesellschaft, Weinheim 1987.
International Search Report of PCT/IB2012/051834 dated Sep. 13, 2012.

* cited by examiner

*Primary Examiner* — Colleen Dunn
*Assistant Examiner* — Haytham Soliman
(74) *Attorney, Agent, or Firm* — Novak Druce Connolly Bove + Quigg LLP

(57) ABSTRACT

The invention relates to a process for producing a catalyst for the oxidation of ethylene to ethylene oxide, which comprises a) providing a support which comprises alumina and has been impregnated with silver or with a silver-comprising compound and has a temperature $T_0$; and b) heating the impregnated support from the temperature $T_0$ to a temperature $T_1$ at a heating rate of at least 30 K/min, and also the catalyst itself which can be obtained by this process.

22 Claims, No Drawings

PROCESS FOR PRODUCING A CATALYST FOR THE OXIDATION OF ETHYLENE TO ETHYLENE OXIDE

CROSS-REFERENCE TO RELATED APPLICATIONS

This application claims benefit (under 35 USC 119(e)) of U.S. Provisional Application 61/475,244, filed Apr. 14, 2011, which is incorporated by reference.

BACKGROUND OF THE INVENTION

The present invention relates to a process for producing a catalyst which is suitable for, in particular, the oxidation of ethylene to ethylene oxide. In the process of the invention, a support which comprises alumina and has been impregnated with an aqueous solution comprising a silver-comprising compound is heated at a heating rate of at least 30 K/min, preferably in a calcination. In a preferred embodiment, this heating is carried out in a belt calciner which has been specifically matched to the process of the invention.

Ethylene oxide is an important basic chemical and in industry is frequently prepared by direct oxidation of ethylene by means of oxygen in the presence of silver-comprising catalysts. Catalysts used are mostly supported catalysts in which the catalytically active, metallic silver has been applied to a support by means of a suitable process. As support material, it is in principle possible to use various porous materials such as activated carbon, titania, zirconia, silica, alumina or ceramic compositions or mixtures of these materials. Particularly preferred supports are based on alpha-alumina.

To improve the activity and/or the selectivity of the catalysts in the oxidation of ethylene to ethylene oxide, promoters are also applied in addition to the active material silver to the support. Mention may be made by way of example of alkali metal and/or alkaline earth metal compounds, tungsten, molybdenum or rhenium, with rhenium being a particularly preferred promoter. For the purposes of the present invention, the term "selectivity" refers to the percentage of the ethylene used in the process which is converted into ethylene oxide in the oxidation. As regards the activity of the catalyst, the activity of the catalyst is higher, the lower the temperature required to achieve a given concentration of ethylene oxide at the reactor outlet under otherwise constant reaction conditions.

To influence the activity and/or the selectivity of such catalysts, various measures are disclosed in the documents of the prior art.

WO 2004/094054 A2 discloses that an impregnated support is activated by firstly increasing the temperature of the support to a value of from 120 to 500° C. and, as soon as the support has a temperature of more than 300° C., keeping the support under an inert gas atmosphere. If lower temperatures of not more than 300° C. are used, it is necessary, according to WO 2004/094054 A2, to carry out the calcination in air.

WO 03/086624 A1 and WO 01/83105 A1 describe the same.

US 2008/0039316 A1 discloses that the calcination should be configured as a 2-stage process. Here, the first calcination is carried out at temperatures up to 270° C. in an air atmosphere, while the second calcination, which is carried out under inert gas, is carried out at temperatures of from 200 to 600° C. As the examples of US 2008/0039316 A1 show, temperatures of 400° C. are reached in the second calcination.

WO 2007/081379 A2 discloses a calcination process in which a furnace having a plurality of heating zones is used. During the disclosed increase of the temperature to 400° C., the catalyst to be calcined passes through a total of 4 zones.

WO 2009/042300 A1 describes calcinations at temperatures of from 200 to 600° C., particularly preferably from 200 to 450° C., and different calcination times of from less than 300 seconds to 8 hours. It is explicitly taught that the calcination time is inconsequential as long as it is ensured that the time is correlated appropriately with the calcination temperature in order to ensure that the silver-comprising compound applied to the support is converted completely to silver. As regards the atmosphere under which the calcination takes place, WO 2009/042300 A1 discloses an inert gas atmosphere having an oxygen content of from 10 ppm to about 21% by volume. According to an example, calcination temperatures of 450° C. are used.

EP 1 210 301 A1 discloses the use of a belt calciner for calcining a catalyst. As calcination atmosphere, supercritical steam is used according to the examples. Part of the supercritical steam used for the calcination is recirculated to the calcination, and part of the steam is replaced by fresh steam.

EP 0 764 464 B1 discloses a process for producing a catalyst, during the production of which a porous support is impregnated with a lithium compound and a cesium compound in a first step and the support which has been impregnated in this way is impregnated with a silver compound and a cesium compound in a second step. A heat treatment is absolutely necessary between the two steps. A further heat treatment has to be carried out after the second impregnation. For the heat treatment, temperatures in the range from 130 to 300° C. are disclosed and generally air, inert gas or superheated steam is disclosed as atmosphere, with superheated steam generally being disclosed as particularly preferred and also being described for both heat treatments in the examples.

EP 0 384 312 A1 describes heat treatment of a catalyst at temperatures of generally from 180 to 300° C., preferably from 220 to 250° C. As can be seen from the examples of EP 0 384 312 A1, a convection oven is preferably used for the heat treatment.

EP 1 086 743 A1 discloses calcination of a catalyst in an inert gas atmosphere at temperatures of from 400 to 700° C. It is explicitly stated that calcination temperatures below 400° C. are not suitable. Contrary to the description, air is used for the calcination in Example 1.

EP 0 804 289 B1 discloses a stepwise impregnation of a support, with the support firstly being impregnated with a silver solution and subsequently being impregnated with an alkali metal solution. It is essential that both the silver solution and the alkali metal solution are essentially free of water. On the basis of these non-aqueous solvents and the stepwise impregnation, it is also stated that the support obtained after the impregnation by means of the water-free alkali metal solution is quite generally dried quickly, with temperatures in the range from 100 to 800° C. and from 200 to 600° C. being described. None of the examples of EP 0 804 289 B1 indicates what temperature increases are actually set during drying after impregnation with alkali metal. In addition, all examples according to the invention relate to embodiments in which the temperature of drying after the impregnation with alkali metal is no higher than 200° C. As regards the preceding drying step, i.e. the drying step after impregnation with silver from water-free solution, rapid drying operations are also described here, with, for example, successive temperatures of 200° C., 300° C. and 400° C. (see, for example, Examples 2, 3, 10) or temperatures of 150° C., 200° C., 250° C., 300° C. and 400° C. (Examples 5 and 6) being employed or the temperature being increased continuously to 400° C. for this drying operation and this heating being carried out in a total of 7 zones of a belt calciner (see, for example, Example 3). Thus, EP 0 804 289 B1 states that it is absolutely necessary for the production of the catalyst on the basis of water-free impregnation solutions to set various, ever higher temperatures of up to 400° C. either in successive steps or in various zones of a belt calciner after impregnation with silver. Examples 8 and 9 disclose that temperatures of up to 500° C. may sometimes be necessary; in the case of such high temperatures of 500° C., the catalyst passes through, for example, seven zones of a belt calciner (Example 11). If the support is impregnated with alkali metal in addition to silver according to EP 0 804 289 B1, a further impregnation step is taught in any case, and this then makes a further drying step absolutely necessary.

It was an object of the present invention to provide an improved process for producing catalysts for the oxidation of ethylene to ethylene oxide.

It has surprisingly been found that catalysts which are very well suited to the oxidation of ethylene to ethylene oxide can be obtained by firstly impregnating a suitable support with silver by means of an aqueous impregnation solution comprising a silver-comprising compound and then subjecting it to rapid heating.

The present invention accordingly provides a process for producing a catalyst for the oxidation of ethylene to ethylene oxide, which comprises
a) impregnating a support comprising alumina with an aqueous solution comprising a silver-comprising compound, and providing the impregnated support at a temperature $T_0$;
b) heating the impregnated support from the temperature $T_0$ to a temperature $T_1$ at a heating rate of at least 30 K/min.

Step a)

In step a), a support comprising alumina is impregnated with an aqueous solution comprising a silver-comprising compound, and the impregnated support is provided at a temperature $T_0$.

Unimpregnated Support

The unimpregnated support preferably comprises from 90 to 99% by weight, more preferably from 92 to 98% by weight, and more preferably from 95 to 97% by weight, based on the total weight of the unimpregnated support, of alumina, calculated as $Al_2O_3$. While all suitable alumina phases are conceivable in principle, for example alpha-alumina, gamma-alumina or theta-alumina or mixed alumina phases, alpha-alumina is particularly preferred for the purposes of the present invention. More preferably, at least 95% by weight, more preferably at least 97% by weight, more preferably at least 99% by weight, more preferably at least 99.9% by weight, of the alumina comprised in the unimpregnated support is alpha-alumina.

The present invention therefore also provides the process as described above, which comprises
a) impregnating a support comprising alumina with an aqueous solution comprising a silver-comprising compound, and providing the impregnated support at a temperature $T_0$, where the unimpregnated support comprises from 95 to 97% by weight, based on the total weight of the unimpregnated support, of alumina, calculated as $Al_2O_3$, and at least 99% by weight of the alumina is alpha-alumina;
b) heating the impregnated support from the temperature $T_0$ to a temperature $T_1$ at a heating rate of at least 30 K/min.

In a further preferred embodiment, the unimpregnated support comprises at least one alkaline metal, with the total alkali metal content of the unimpregnated support preferably being in the range up to 2500 ppm, preferably from 10 to 2500 ppm, more preferably from 50 to 1000 ppm, in each case based on the total weight of the unimpregnated support and calculated as element.

The unimpregnated support particularly preferably comprises sodium and/or potassium, more preferably sodium and potassium.

If the unimpregnated support comprises sodium, the sodium content is preferably in the range from 10 to 1500 ppm, more preferably from 10 to 800 ppm, more preferably from 10 to 600 ppm, more preferably from 10 to 500 ppm, based on the total weight of the unimpregnated support and calculated as Na.

If the unimpregnated support comprises potassium, the potassium content is preferably not more than 1000 ppm, more preferably not more than 500 ppm, more preferably not more than 200 ppm, for example in the range from 10 to 200 ppm, based on the total weight of the unimpregnated support and calculated as K.

In a further preferred embodiment, the unimpregnated support comprises at least one alkaline earth metal, with the total alkaline earth metal content of the unimpregnated support preferably being up to 2500 ppm, for example in the range from 1 to 2500 ppm, more preferably from 10 to 1200 ppm, more preferably from 100 to 800 ppm, in each case based on the total weight of the support and calculated as element.

The unimpregnated support particularly preferably comprises calcium and/or magnesium, more preferably calcium and magnesium.

If the unimpregnated support comprises calcium, the calcium content is preferably in the range from 10 to 1500 ppm, more preferably from 20 to 1000 ppm, more preferably from 30 to 600 ppm, in each case based on the total weight of the unimpregnated support and calculated as element.

If the unimpregnated support comprises magnesium, the magnesium content is preferably in the range up to 800 ppm, preferably from 1 to 500 ppm, more preferably from 1 to 250 ppm, more preferably from 1 to 100 ppm, in each case based on the total weight of the unimpregnated support and calculated as element.

In a preferred embodiment, the unimpregnated support comprises silicon in an amount in the range from 50 to 10000 ppm, preferably from 100 to 5000 ppm, more preferably from 100 to 2500 ppm, in each case based on the total weight of the unimpregnated support and calculated as Si.

In one embodiment, the unimpregnated support comprises zinc in an amount in the range from 10 to 1500 ppm, preferably from 10 to 750 ppm, more preferably from 10 to 300 ppm, in each case based on the total weight of the unimpregnated support and calculated as Zn.

In one embodiment, the unimpregnated support comprises zirconium in an amount in the range from 1 to 10000 ppm, preferably from 10 to 8000 ppm, more preferably from 10 to 6000 ppm, more preferably from 10 to 5000 ppm, in each case based on the total weight of the unimpregnated support and calculated as Zr.

In one embodiment, the unimpregnated support comprises both zinc in an amount in the range from 10 to 1500 ppm, preferably from 10 to 750 ppm, more preferably from 10 to 300 ppm, and zirconium in an amount in the range from 1 to 10000 ppm, preferably from 10 to 8000 ppm, more preferably from 10 to 6000 ppm, more preferably from 10 to 5000 ppm, in each case based on the total weight of the unimpregnated support and calculated as Zn and Zr.

In another embodiment, the unimpregnated support comprises less than 10 ppm of zinc and less than 1 ppm of zirconium; in this embodiment, the unimpregnated support preferably comprises both zinc and zirconium in an amount below the respective detection limit or is free of both zinc and zirconium.

In a preferred embodiment of the present invention, the unimpregnated support has a BET surface area determined in accordance with DIN ISO 9277 in the range from 0.1 to 5 $m^2/g$, more preferably in the range from 0.2 to 2 $m^2/g$, more preferably in the range from 0.3 to 1.5 $m^2/g$, more preferably in the range from 0.4 to 1.4 $m^2/g$, more preferably in the range from 0.5 to 1.3 $m^2/g$, more preferably in the range from 0.6 to 1.2 $m^2/g$ and particularly preferably in the range from 0.7 to 1.0 $m^2/g$.

In a preferred embodiment of the present invention, the unimpregnated support has pores having diameters in the range from 0.1 to 100 μm, with the pore distribution preferably being monomodal or polymodal, more preferably polymodal, particularly preferably bimodal. In the particularly preferred bimodal pore distribution, the peak maxima obtained by determining the pore diameters by means of Hg porosimetry in accordance with DIN 66133 are more preferably in the range from 0.1 to 10 μm and from 15 to 100 μm, preferably in the range from 0.1 to 5 μm and from 17 to 80 μm, more preferably in the range from 0.1 to 3 μm and from 20 to 70 μm, more preferably in the range from 0.1 to 2.5 μm and from 20 to 65 μm.

The present invention therefore also provides the process as described above, which comprises a) impregnating a support comprising alumina with an aqueous solution comprising a silver-comprising compound, and providing the impregnated support at a temperature $T_0$, where the unimpregnated support comprises from 95 to 97% by weight, based on the total weight of the unimpregnated support, of alumina, calculated as $Al_2O_3$, and at least 99% by weight of the alumina is alpha-alumina, and the unimpregnated support has a BET surface area determined in accordance with DIN ISO 9277 in the range from 0.1 to 5 $m^2/g$, in particular in the range from 0.7 to 1.0 $m^2/g$;

b) heating the impregnated support from the temperature $T_0$ to a temperature $T_1$ at a heating rate of at least 30 K/min.

The present invention likewise provides the process as described above, which comprises a) impregnating a support comprising alumina with an aqueous solution comprising a silver-comprising compound, and providing the impregnated support at a temperature $T_0$, where the unimpregnated support comprises from 95 to 97% by weight, based on the total weight of the unimpregnated support, of alumina, calculated as $Al_2O_3$, and at least 99% by weight of the alumina is alpha-alumina, and the unimpregnated support has a bimodal pore distribution in which the peak maxima determined by Hg porosimetry in accordance with DIN 66133 are in the range from 0.1 to 10 μm and from 15 to 100 μm, in particular in the range from 0.1 to 2.5 μm and from 20 to 65 μm;

b) heating the impregnated support from the temperature $T_0$ to a temperature $T_1$ at a heating rate of at least 30 K/min.

The present invention preferably also provides the process as described above, which comprises a) impregnating a support comprising alumina with an aqueous solution comprising a silver-comprising compound, and providing the impregnated support at a temperature $T_0$, where the unimpregnated support comprises from 95 to 97% by weight, based on the total weight of the unimpregnated support, of alumina, calculated as $Al_2O_3$, and at least 99% by weight of the alumina is alpha-alumina, and the unimpregnated support has a bimodal pore distribution in which the peak maxima determined by Hg porosimetry in accordance with DIN 66133 are in the range from 0.1 to 10 μm and from 15 to 100 μm, in particular in the range from 0.1 to 2.5 μm and from 20 to 65 μm, and the unimpregnated support has a BET surface area determined in accordance with DIN ISO 9277 in the range from 0.1 to 5 $m^2/g$, in particular in the range from 0.7 to 1.0 $m^2/g$;

b) heating the impregnated support from the temperature $T_0$ to a temperature $T_1$ at a heating rate of at least 30 K/min.

The geometric shape of the unimpregnated support used according to the invention can in principle be chosen at will and can in principle be matched to the specific requirements which the catalyst has to meet when used in the gas-phase oxidation of ethylene to ethylene oxide. The support advantageously has a geometry which allows unhindered diffusion of the reaction gases used and occurring in this reaction to a very large proportion of the external and internal area of the support which is coated with silver particles and optionally coated with further promoters.

In a preferred embodiment, the support used according to the invention has the geometry of a rod, for example a hollow rod, a star, a sphere, a ring, or a cylinder. According to the invention, preference is given to using a support which has the geometry of a cylinder. Further preference is given to a support which has the geometry of a cylinder having a length in the range from 5 to 10 mm, an external diameter in the range from 5 to 10 mm and a ratio of external diameter in mm to wall thickness in mm in the range from 2.5 to 4.5. Particular preference is given to cylinders having the following geometries (external diameter×length×internal diameter, in each case in mm): 5×5×2, 6×6×3, 7×7×3, 8×8×3, 8×8.5×3, 8×8.5× 3.5, 8.5×8×3.5, 8.5×8×3, 9×9×3, 9.5×9×3, 9.5×9×3.5. Each length indicated comprises tolerances in the region of ±0.5 mm.

The impregnation of the support is, as described above, carried out by means of an aqueous solution comprising a silver-comprising compound. For the purposes of the present invention, particular preference is given to vacuum impregnation. In this vacuum impregnation, the support is preferably firstly subjected to a vacuum treatment in which the support is exposed to a pressure in the region of preferably not more than 500 mbar, more preferably not more than 250 mbar, more preferably not more than 100 mbar, for example from 10 to 100 mbar or from 20 to 100 mbar. The vacuum treatment is preferably carried out at a temperature in the range from 1 to 80° C., more preferably from 3 to 50° C., more preferably from 5 to 30° C. and particularly preferably at room temperature. The vacuum treatment is preferably carried out for a period of at least 1 minute, preferably at least 5 minutes, more preferably for a period in the range from 5 to 120 minutes, more preferably from 10 to 45 minutes, more preferably from 15 to 30 minutes. After the vacuum treatment, the support is brought into contact with the aqueous solution comprising the silver-comprising compound to effect impregnation. Here, the aqueous solution is preferably dripped or sprayed onto the support, more preferably dripped.

As regards the chemical nature of the silver-comprising compound, there are in principle no restrictions as long as it is ensured that the silver can be applied in a suitable way to the support by means of the aqueous solution comprising this compound. It is likewise possible for the aqueous solution to comprise two or more different, silver-comprising compounds. According to the invention, preference is given to using Ag(I) oxide or Ag(I) oxalate as silver-comprising compounds, with Ag(I) oxalate being particularly preferred.

If required, the aqueous solution can comprise a complexing agent in addition to the silver-comprising compound. Preferred complexing agents are amines such as ethanolamine or ethylenediamine. Particular preference is given to ethylenediamine. If the aqueous solution comprises such a complexing agent, the silver in the aqueous solution is at least partly present in the form of the corresponding silver complex.

As regards the concentration of the silver-comprising compound in the aqueous solution, this is preferably in the range from 25 to 35% by weight, more preferably in the range from 27 to 32% by weight, and more preferably in the range from 28 to 30% by weight. The impregnation according to the invention preferably produces an impregnated support having a silver content, calculated as elemental Ag, in the range from 1 to 50% by weight, preferably in the range from 5 to 35% by weight, and more preferably in the range from 10 to 25% by weight, in each case based on the weight of the support which has been calcined according to the invention.

In a particularly preferred embodiment of the process of the invention, the impregnation of the support as per a) provides an impregnated support which comprises at least one promoter in addition to silver. Preferred promoters are, for instance, rhenium, tungsten, lithium, cesium, and sulfur. In principle, each of these promoters can be applied in a suitable form separately from silver to the support. It is conceivable, for example, for each promoter to be applied in a separate impregnation step. Either a drying step and/or a calcination step can essentially be carried out between the individual impregnation steps.

The present invention therefore also provides the process as described above in which, in step a), the support comprising alumina is additionally impregnated with rhenium or with a rhenium-comprising compound, preferably also with tungsten or with a tungsten-comprising compound and/or with lithium or with a lithium-comprising compound and/or with cesium or with a cesium-comprising compound, and the support is optionally impregnated with sulfur or with a sulfur-comprising compound.

However, particular preference is given in the present invention to applying the promoter or promoters together with silver to the support in a single step by impregnating the support with an aqueous solution comprising the silver-comprising compound and also a compound comprising the promoter or compounds comprising promoters.

The present invention therefore preferably provides the process as described above in which, in step a), the aqueous solution comprising a silver-comprising compound additionally comprises a rhenium-comprising compound, a tungsten-comprising compound, a lithium-comprising compound, a cesium-comprising compound, and optionally a sulfur-comprising compound.

The process of the invention is therefore characterised by, inter alia, the unimpregnated support being, in step a), impregnated in a single step by means of a single aqueous solution comprising both silver and also all promoters, in particular rhenium, tungsten, lithium, cesium and optionally sulfur, which the catalyst ultimately obtained is to comprise. Since the unimpregnated support is impregnated not only with silver but also with the promoters in this single step, any intermediate treatments such as drying or calcination which can occur in processes having a plurality of impregnation steps become unnecessary.

The present invention therefore provides a process as described above in which, during step a), both silver and all promoters, preferably rhenium, tungsten, lithium, cesium and optionally sulfur, are applied by impregnation in a single impregnation step and no drying and no calcination is carried out during step a) and after step a) the impregnated support is subjected exclusively to the heat treatment according to steps b) and optionally c) and d) as described below.

The aqueous solution by means of which both silver and the promoters are applied by impregnation to the support in step a) of the process of the invention preferably comprises a halide, an oxyhalide, an oxide, an acid or a salt of a heteropolyacid of rhenium, for example a rhenate or perrhenate, as rhenium-comprising compound. The rhenium-comprising compound is preferably a compound selected from the group consisting of ammonium perrhenate, rhenium(III) chloride, rhenium(V) chloride, rhenium(V) fluoride, rhenium(VI) oxide and rhenium(VII) oxide. Particular preference is given to ammonium perrhenate. As regards the concentration of the rhenium-comprising compound in the aqueous solution, this is preferably in the range from 1 to 5% by weight, more preferably in the range from 2 to 4.5% by weight and more preferably in the range from 2.8 to 4.2% by weight, of rhenium, in each case calculated as element. The impregnation according to the invention preferably produces an impregnated support having a rhenium content, calculated as elemental Re, in the range from 100 to 1000 ppm, preferably in the range from 100 to 600 ppm and more preferably in the range from 250 to 500 ppm, in each case based on the weight of the support which has been calcined according to the invention.

The aqueous solution by means of which both silver and the promoters are applied by impregnation to the support in step a) of the process of the invention preferably comprises a tungsten salt or tungstic acid as tungsten-comprising compound. Particular preference is given to tungstic acid. As regards the concentration of the tungsten-comprising compound in the aqueous solution, this is preferably in the range from 0.1% by weight to 5% by weight, more preferably in the range from 0.5% by weight to 3% by weight and more preferably in the range from 0.8% by weight to 2.5% by weight, of tungsten, in each case calculated as element. The impregnation according to the invention preferably produces an impregnated support having a tungsten content, calculated as elemental W, in the range from 10 to 500 ppm, preferably in the range from 50 to 300 ppm and more preferably in the range from 80 to 250 ppm, in each case based on the weight of the support which has been calcined according to the invention.

The aqueous solution by means of which both silver and the promoters are applied by impregnation to the support in step a) of the process of the invention preferably comprises an at least partially water-soluble lithium salt as lithium-comprising compound. Particular preference is given to lithium nitrate. As regards the concentration of the lithium-comprising compound in the aqueous solution, this is preferably in the range from 0.5 to 5% by weight, more preferably in the range from 1 to 4% by weight and more preferably in the range from 1.5 to 3% by weight, of lithium calculated as element. The impregnation according to the invention preferably produces an impregnated support having a lithium content, calculated as elemental Li, in the range from 10 to 500 ppm, preferably in the range from 50 to 400 ppm and more preferably in the range from 100 to 250 ppm, in each case based on the weight of the support which has been calcined according to the invention.

The aqueous solution by means of which both silver and the promoters are applied by impregnation to the support in step a) of the process of the invention preferably comprises an at least partially water-soluble cesium salt as cesium-comprising compound. Particular preference is given to cesium hydroxide. As regards the concentration of the cesium-comprising compound in the aqueous solution, this is preferably in the range from 0.5 to 6% by weight, more preferably in the range from 1.5 to 5.5% by weight and more preferably in the range from 3% by weight to 5% by weight, of cesium calculated as element. The impregnation according to the invention preferably produces an impregnated support having a cesium content, calculated as elemental Cs, in the range from 100 to 800 ppm, preferably in the range from 200 to 700 ppm and more preferably in the range from 250 to 600 ppm, in each case based on the weight of the support which has been calcined according to the invention.

The aqueous solution by means of which both silver and the promoters are applied by impregnation to the support in step a) of the process of the invention preferably comprises ammonium sulfate as optional sulfur-comprising compound. As regards the concentration of the sulfur-comprising compound in the aqueous solution, this is preferably in the range from 0.05 to 0.5% by weight, more preferably in the range from 0.1 to 0.35% by weight and more preferably in the range from 0.15 to 0.3% by weight, of sulfur calculated as element. The impregnation according to the invention preferably produces an impregnated support having a sulfur content, calculated as elemental S, in the range from 0 to 50 ppm, preferably in the range from 2 to 30 ppm and more preferably in the range from 5 to 20 ppm, in each case based on the weight of the support which has been calcined according to the invention.

In a preferred embodiment of the process of the invention, the impregnation solution is produced from a solution comprising tungsten and cesium, a solution comprising lithium and sulfur and a solution comprising rhenium. These three solutions comprise the promoters mentioned in such amounts that mixing of the three solutions gives an impregnation solution which comprises the promoters in the abovementioned amounts.

Temperature $T_0$

In step a) of the process of the invention, the above-described support comprising alumina and impregnated with silver or with a silver-comprising compound is provided at a temperature $T_0$. Should the impregnated support be obtained at a temperature of greater than $T_0$ in the impregnation, in particular in the particularly preferred single-step impregnation, it is, according to the invention, firstly cooled to the temperature $T_0$.

Temperatures $T_0$ in the range up to 35° C., for example in the range up to 30° C., are in principle conceivable. The temperature $T_0$ is preferably in the range from 5 to 20° C., more preferably in the range from 5 to 15° C.

In preferred embodiments of the invention, the temperature $T_0$ is such that the support provided in step a) does not have to be subjected to predrying after the impregnation as described above before it is heated according to the invention at a heating rate of at least 30 K/min in step b).

The present invention therefore preferably provides a process in which the catalyst obtained after the impregnation as described above of the support is not subjected to a temperature greater than 35° C., preferably greater than 30° C., more preferably greater than 25° C. and more preferably greater than 20° C., before heating at a heating rate of at least 30 K/min.

Step b)

In step b) of the process of the invention, the impregnated support provided at the temperature $T_0$ is heated at a heating rate of at least 30 K/min.

Heating rates of up to 150 K/min, for example up to 100 K/min or up to 80 K/min are conceivable in principle. The heating rate in step b) is preferably in the range from 30 to 80 K/min, more preferably in the range from 30 to 75 K/min, more preferably in the range from 30 to 70 K/min.

In step b) of the process of the invention, the support is heated from the temperature $T_0$ to the temperature $T_1$.

According to the invention, the support is heated to temperatures $T_1$ which are suitable for calcination of the impregnated support. Here, temperatures $T_1$ of up to 350° C., for example up to 340° C. or up to 330° C. or up to 320° C. or up to 310° C. or up to 300° C., are conceivable in principle. Preferred minimal temperatures $T_1$ are in the region of 250° C. Accordingly, temperatures $T_1$ in the range from 250 to 310° C. or in the range from 250 to 300° C. are conceivable. However, it has been found, according to the invention, that it is possible to set calcination temperatures of less than 300° C. The present invention therefore provides the process as described above in which the temperature $T_1$ is less than 300° C., preferably less than or equal to 299° C.

According to the invention, the temperature $T_1$ is preferably in the range from 250 to 295° C., more preferably in the range from 260 to 295° C., more preferably in the range from 270 to 295° C., more preferably in the range from 270 to 290° C., for example in the range from 270 to 285° C., from 275 to 290° C., or from 275 to 285° C.

As regards the way in which the heating rate according to the invention is achieved, there are in principle no restrictions. During heating of the supports present at the temperature $T_0$, the support is preferably brought into contact with a gas and the heating of the support is more preferably effected by means of this gas and the gas thus has a temperature which allows the support to be heated to the temperature $T_1$.

As regards the chemical composition of the gas which is brought into contact with the support during heating of the support, there are in principle no restrictions. It is, for instance, conceivable for the gas to comprise oxygen, for example in concentrations of up to 100% by volume or up to 25% by volume based on the gas. It is thus conceivable, for example, to use air. Lower oxygen contents are also conceivable and, for example, mixtures of nitrogen and air, e.g. lean air, are conceivable. Mention may be made of oxygen contents of the gas of up to 20% by volume or up to 15% by volume or up to 10% by volume or up to 5% by volume or up to 1% by volume. For the purposes of the present invention, particular preference is given to using an inert gas or a mixture of two or more inert gases as gas for heating, with the oxygen content preferably being less than 10 ppm, more preferably in the range from 5 to 9 ppm. As inert gases, mention may be made by way of example of nitrogen, carbon dioxide, argon and/or helium. Particular preference is given to using nitrogen as inert gas for the purposes of the present invention.

The present invention accordingly provides the process as described above in which the heating in b) is effected by bringing the support into contact with an inert gas $I_1$.

The present invention preferably provides the process as described above in which the heating in b) is effected by bringing the support into contact with an inert gas $I_1$, where the inert gas comprises less than 10 ppm, preferably from 5 to 9 ppm, of oxygen.

The present invention more preferably provides the process as described above in which the heating in b) is effected by bringing the support into contact with an inert gas $I_1$, where the inert gas is nitrogen and the inert gas comprises less than 10 ppm, preferably from 5 to 9 ppm, of oxygen.

The expression "inert gas $I_1$ comprising less than 10 ppm, preferably from 5 to 9 ppm, of oxygen" here refers to a gas mixture comprising the inert gas $I_1$ and oxygen, where the oxygen content of less than 10 ppm or from 5 to 9 ppm relates to the oxygen content of the gas mixture and the inert gas $I_1$ can be a mixture of 2 or more inert gases.

For the purposes of the present invention, very particular preference is given to using technical-grade nitrogen, preferably obtained from fractionation of air, which typically comprises nitrogen in the range from 99.995 to 99.9999% by volume, oxygen in the range from 6 to 8 ppm and traces of noble gases as gas with which the support is brought into contact during heating in step b).

The temperature of the gas with which the support is brought into contact during heating is basically selected so that the heating rates according to the invention can be made possible and the support can be brought to the temperature $T_1$. The gas with which the support is brought into contact during heating in step b) preferably has a temperature in the range from $T_1$ to 1.1 $T_1$, more preferably in the range from $T_1$ to 1.07 $T_1$, more preferably in the range from $T_1$ to 1.05 $T_1$.

The contacting of the support with the gas in step b) can in principle be carried out in any desired way as long as it is ensured that the heating rate according to the invention of the support is achieved. In this respect, the support is particularly preferably brought into contact with a stream of the gas, preferably a stream of the inert gas $I_1$, i.e. the gas is passed through the support. Here, the volume flow of the gas is basically selected so that the heating rate according to the invention is achieved. In particular, the volume flow of the gas is selected so that the combination of the temperature and the volume flow of the gas, which is brought into contact with the support, achieves the heating rate according to the invention. The volume flow is particularly preferably in the range from 2500 to 5000 m³/h, more preferably from 3200 to 4500 m³/h.

In a preferred embodiment, the present invention provides the process as described above in which an inert gas $I_1$, preferably nitrogen, is passed through the support to be heated according to b), where $I_1$ preferably comprises less than 10 ppm, more preferably from 5 to 9 ppm, of oxygen, $I_1$ preferably has a temperature in the range from $T_1$ to 1.1 $T_1$ and $I_1$ preferably flows through the support at a volume flow in the range from 2500 to 5000 m³/h, more preferably from 3200 to 4500 m³/h.

During heating of the support according to step b), the heating rate can be constant or can vary as long as it is ensured that the overall heating rate calculated from the temperature difference ($T_1-T_0$) divided by the total time required for heating is at least 30 K/min and preferably in the range from 30 to 80 K/min, more preferably in the range from 30 to 75 K/min, more preferably in the range from 30 to 70 K/min. The heating rate during the total heating operation is preferably at least 30 K/min, more preferably in the range from 30 to 80 K/min, more preferably in the range from 30 to 75 K/min, more preferably in the range from 30 to 70 K/min.

Ranges of the heating rate which are possible according to the invention are, for example, from 35 to 80 K/min or from 40 to 75 K/min or from 40 to 70 K/min or from 45 to 70 K/min or from 50 to 70 K/min or from 55 to 70 K/min or from 60 to 70 K/min or from 65 to 70 K/min.

Step c)

In a preferred embodiment, the support which has been heated to the temperature $T_1$ is, after heating, preferably directly after heating, maintained at a temperature $T_2$ which is suitable for the purposes of the calcination according to the invention. Preference is given here to temperatures $T_2$ which are in the region of the temperature $T_1$. Particular preference is given to temperatures $T_2$ which are in the range from 0.90 to 1.1 $T_1$, for example in the range from 0.95 to 1.05 $T_1$, from 0.96 to 1.04 $T_1$, from 0.97 to 1.03 $T_1$, from 0.98 to 1.02 $T_1$ or from 0.99 to 1.01 $T_1$. The temperature $T_2$ is preferably selected so that it is less than 300° C., preferably less than or equal to 299° C.

The present invention therefore also provides the process as described above, which further comprises c) maintaining the support which has been heated to the temperature $T_1$ at a temperature $T_2$ which is preferably in the range from 0.90 $T_1$ to 1.1 $T_1$, where, more preferably, the temperature $T_2$ is less than 300° C., preferably less than or equal to 299° C.

Maintaining the support at the temperature $T_2$ also comprises embodiments in which the value of $T_2$ is not constant during the hold time but instead varies within the above-described limits. The present invention therefore also comprises, inter alia, embodiments in which the support is maintained at two or more different temperatures within the above-described limits for $T_2$.

The time for which the support is maintained at the temperature $T_2$ is in principle not subject to any restrictions. For the purposes of the present invention, preference is given to the support being maintained at the temperature $T_2$ for a time in the range from 1 to 15 minutes, preferably from 2 to 10 minutes, more preferably from 3 to 5 minutes, in c).

As regards the way in which the support is maintained according to the invention at the temperature $T_2$ in step c), there are in principle no restrictions. While being maintained at the temperature $T_2$, the support is preferably brought into contact with a gas having a temperature which allows the support to be maintained at the temperature $T_2$.

As regards the chemical composition of the gas with which the support is brought into contact in order to maintain the support at the temperature $T_2$, there are in principle no restrictions. Thus, it is conceivable, for instance, for the gas to comprise oxygen in an amount of up to 100% by volume or up to 25% by volume based on the gas. It is thus conceivable, for example, to use air. Lower contents of oxygen are also conceivable, with, for example, mixtures of nitrogen and air, e.g. lean air, being conceivable. Mention may be made of oxygen contents of gas of up to 20% by volume or up to 15% by volume or up to 10% by volume or up to 5% by volume or up to 1% by volume. For the purposes of the present invention, particular preference is given to using an inert gas or a mixture of two or more inert gases in which the oxygen content is preferably less than 10 ppm, more preferably in the range from 5 to 9 ppm, as gas for maintaining the support at the temperature $T_2$. As inert gases, mention may be made by way of example of nitrogen, carbon dioxide, argon and helium. For the purposes of the present invention, particular preference is given to using nitrogen as inert gas.

The present invention accordingly provides the process as described above in which the support is maintained at the temperature $T_2$ according to c) by bringing the support into contact with an inert gas $I_2$.

The present invention preferably provides the process as described above in which the support is maintained at the temperature $T_2$ according to c) by bringing the support into contact with an inert gas $I_2$ comprising less than 10 ppm, preferably from 5 to 9 ppm, of oxygen.

The present invention more preferably provides the process as described above in which the support is maintained at the temperature $T_2$ according to c) by bringing the support into contact with an inert gas $I_2$, where the inert gas is nitrogen and the inert gas comprises less than 10 ppm, preferably from 5 to 9 ppm, of oxygen.

The expression "inert gas $I_2$ comprising less than 10 ppm, preferably from 5 to 9 ppm, of oxygen" here refers to a gas mixture comprising the inert gas $I_2$ and oxygen, where the oxygen content of less than 10 ppm or from 5 to 9 ppm relates to the oxygen content of the gas mixture and the inert gas $I_2$ can be a mixture of two or more inert gases.

For the purposes of the present invention, very particular preference is given to using technical-grade nitrogen, preferably obtained from fractionation of air, which typically comprises nitrogen in the range from 99.995 to 99.9999% by volume, oxygen in the range from 6 to 8 ppm, and traces of noble gases as gas with which the support is brought into contact during maintenance of the support at the temperature $T_2$ in step c).

The present invention therefore provides the process as described above in which the support is maintained at the temperature $T_2$ according to c) by means of an inert gas $I_2$, preferably by means of nitrogen, where the inert gas $I_2$ preferably comprises less than 10 ppm, more preferably from 5 to 9 ppm, of oxygen.

The temperature of the gas with which the support is brought into contact to maintain the support at the temperature $T_2$ according to c) is basically selected so that the hold temperature according to the invention is made possible. The gas with which the support is to be brought into contact to maintain it at the temperature $T_2$ in step c) preferably has a temperature in the range from $T_2$ to 1.1 $T_2$, more preferably in the range from $T_2$ to 1.07 $T_2$, more preferably in the range from $T_2$ to 1.05 $T_2$, for example in the range from $T_2$ to 1.04 $T_2$ or in the range from $T_2$ to 1.03 $T_2$ or in the range from $T_2$ to 1.02 $T_2$ or in the range from $T_2$ to 1.01 $T_2$.

The contacting of the support with the gas in step c) can in principle be carried out in any way as long as it is ensured that the support is maintained at the temperature $T_2$ according to the invention. In this respect, particular preference is given to bringing the support into contact with a stream of the gas, preferably with a stream of the inert gas $I_2$, i.e. to pass the gas through the support. Here, the volume flow of the gas is selected essentially so that the support is maintained at the temperature $T_2$ according to the invention. In particular, the volume flow of the gas is selected so that the combination of the temperature and the volume flow of the gas which is brought into contact with the support maintains the support at the temperature $T_2$ according to the invention. The volume flow is particularly preferably in the range from 1000 to 3000 m³/h, more preferably from 1500 to 2000 m³/h.

In a preferred embodiment, the present invention provides the process as described above in which an inert gas $I_2$, preferably nitrogen, is passed through the support to be maintained at the temperature $T_2$ according to c), where $I_2$ preferably comprises less than 10 ppm, more preferably from 5 to 9 ppm, of oxygen, $I_2$ preferably has a temperature in the range from $T_2$ to 1.05 $T_2$ and $I_2$ preferably flows through the support at a volume flow in the range from 1000 to 3000 m³/h, more preferably from 1500 to 2000 m³/h.

For the purposes of the present invention, the inert gas $I_1$ is preferably, but not necessarily, used as inert gas $I_2$; as described above, the volume flow of $I_2$ can be different from the volume flow of $I_1$ and/or the temperature of $I_2$ can be different from the temperature of $I_1$.

Step d)

In a preferred embodiment, the support which has been maintained at the temperature $T_2$ is, after the hold time, preferably directly after the hold time, cooled to a temperature $T_3$. There are in principle no particular restrictions with regard to the value for $T_3$. Temperatures $T_3$ of not more than 60° C. are preferred for the purposes of the present invention.

The present invention therefore provides the process as described above, which further comprises d) cooling the support which has been maintained at the temperature $T_2$ to a temperature $T_3$ which is not more than 60° C.

As regards the way in which the cooling according to the invention is achieved in step d), there are in principle no restrictions. During cooling to the temperature $T_3$, the support is preferably brought into contact with a gas which has a temperature which allows the support to be cooled to the temperature $T_3$.

As regards the chemical composition of the gas which is brought into contact with the support in order to cool the support to the temperature $T_3$, there are in principle no restrictions. Thus, for example, it is conceivable for an inert gas as is used, for example, in steps b) or c) to be used as gas. For the purposes of the present invention, particular preference is given to using a gas having an oxygen content of at least 5% by volume, preferably at least 10% by volume, more preferably at least 15% by volume, more preferably at least 20% by volume, as gas for cooling to the temperature $T_3$. Particularly preferably, air is used according to the invention for cooling according to d).

The present invention therefore provides the process as described above in which cooling according to d) is carried out in an atmosphere comprising at least 5% by volume, preferably at least 15% by volume, of oxygen, more preferably in air.

According to the invention, the support is preferably cooled in step d) at a cooling rate in the range from 30 to 80 K/min, preferably in the range from 40 to 60 K/min, more preferably in the range from 45 to 55 K/min.

After step d), the calcined and cooled support obtained in this way can either be used immediately as catalyst or can be stored under appropriate conditions.

In a preferred embodiment, the present invention provides a process for producing a catalyst for the oxidation of ethylene to ethylene oxide, which comprises
a) providing a support which comprises alumina and has been impregnated with silver or with a silver-comprising compound and has a temperature $T_0$;
b) heating the impregnated support from the temperature $T_0$ to a temperature $T_1$ at a heating rate of at least 30 K/min, where the temperature $T_1$ is less than 300° C. and heating is effected by bringing the support into contact with an inert gas $I_1$, where the inert gas is nitrogen and the inert gas comprises less than 10 ppm of oxygen.

In a preferred embodiment, the present invention also provides a process for producing a catalyst for the oxidation of ethylene to ethylene oxide, which comprises
a) providing a support which comprises alumina and has been impregnated with silver or with a silver-comprising compound and has a temperature $T_0$;
b) heating the impregnated support from the temperature $T_0$ to a temperature $T_1$ at a heating rate of at least 30 K/min, where the temperature $T_1$ is less than 300° C. and heating is effected by bringing the support into contact with an inert gas $I_1$, where the inert gas is nitrogen and the inert gas comprises less than 10 ppm of oxygen;
c) maintaining the support which has been heated to the temperature $T_1$ at a temperature $T_2$, where $T_2$ is less than 300° C. and the support is maintained at the temperature $T_2$ by bringing the support into contact with an inert gas $I_2$, where the inert gas is nitrogen and the inert gas comprises less than 10 ppm of oxygen.

In a preferred embodiment, the present invention also provides a process for producing a catalyst for the oxidation of ethylene to ethylene oxide, which comprises
a) providing a support which comprises alumina and has been impregnated with silver or with a silver-comprising compound and has a temperature $T_0$ in the range from 5 to 15° C.;
b) heating the impregnated support from the temperature $T_0$ to a temperature $T_1$ in the range from 275 to 285° C. at a heating rate of from at least 30 to 70 K/min, where heating is effected by bringing the support into contact with an inert gas $I_1$, where the inert gas is nitrogen and the inert gas comprises from 5 to 9 ppm of oxygen;

c) maintaining the support which has been heated to the temperature $T_1$ at a temperature $T_2$, where $T_2$ is in the range from $0.90\,T_1$ to $1.1\,T_1$ and the support is maintained at the temperature $T_2$ by bringing the support into contact with an inert gas $I_2$, where the inert gas is nitrogen and the inert gas comprises from 5 to 9 ppm of oxygen.

In a preferred embodiment, the present invention also provides a process for producing a catalyst for the oxidation of ethylene to ethylene oxide, which comprises a) providing a support which comprises alumina and has been impregnated with silver or with a silver-comprising compound and has a temperature $T_0$ in the range from 5 to 15° C.;

b) heating the impregnated support from the temperature $T_0$ to a temperature $T_1$ in the range from 275 to 285° C. at a heating rate of from at least 30 to 70 K/min, where heating is effected by bringing the support into contact with an inert gas $I_1$, where the inert gas is nitrogen and the inert gas comprises from 5 to 9 ppm of oxygen;

c) maintaining the support which has been heated to the temperature $T_1$ at a temperature $T_2$, where $T_2$ is in the range from $0.90\,T_1$ to $1.1\,T_1$ and the support is maintained at the temperature $T_2$ by bringing the support into contact with an inert gas $I_2$, where the inert gas is nitrogen and the inert gas comprises from 5 to 9 ppm of oxygen;

d) cooling the support which has been maintained at the temperature $T_2$ to a temperature $T_3$, where $T_3$ is not more than 60° C. and cooling according to d) is carried out in an atmosphere comprising at least 15% by volume of oxygen.

It has surprisingly been found that the support which has been heated in step a) at the high heating rate according to the invention, in particular the support which has been heated in the inert gas atmosphere as described above, has advantageous properties as catalyst in the oxidation of ethylene to ethylene oxide.

The present invention therefore also provides a catalyst for the oxidation of ethylene to ethylene oxide which can be obtained or has been obtained by a process as described above.

The present invention likewise provides a process for preparing ethylene oxide by gas-phase oxidation of ethylene by means of molecular oxygen in a fixed-bed reactor in the presence of this catalyst.

Belt Calciner

As regards the apparatus employed for the process of the invention, there are essentially no restrictions as long as it is ensured that the heating according to the invention in b), preferably also the maintenance of the temperature according to the invention in c), preferably also the cooling according to the invention in d), can be carried out as described above. According to the invention, preference is given to embodiments in which at least the heating according to b), preferably the heating according to b) and the maintenance of the temperature according to c) and optionally also the cooling according to d) are carried out continuously. Particularly preferably, at least step b), preferably at least steps b) and c), of the process of the invention are carried out in a belt calciner.

In principle, the belt calciner which is preferably used according to the invention can have one or more heating zones in which step b) is carried out. If the belt calciner has a plurality of heating zones, it is possible to use the same gases, preferably inert gases $I_1$, which can have different oxygen contents and/or different temperatures in each of the individual heating zones, with different volume flows of the gases being able to be set in the individual heating zones. According to the invention, it has been found that, owing to the high heating rate of at least 30 K/min, it is sufficient for the belt calciner used to have only a single heating zone, which means that the heating zone of the belt calciner is less complicated to construct in terms of apparatus.

Furthermore, the belt calciner which is preferably used according to the invention can have one or more hold zones in which step c) is carried out. If the belt calciner has a plurality of hold zones, it is possible to use the same gases, preferably inert gases $I_2$, which can have different oxygen contents and/or different temperatures in each of the individual hold zones, with different volume flows of the gases being able to be set in the individual hold zones. According to the invention, it has been found that it is sufficient for the belt calciner used to have only a single hold zone, which means that not only the heating zone but also the hold zone of the belt calciner is less complicated to construct. For the purposes of the present invention, particular preference is given to the hold zone or the first of the plurality of hold zones in the belt calciner being provided directly after the heating zone or the last of the plurality of heating zones.

As regards the preferred parameters in the heating according to step b) and the maintenance of the temperature according to step c), reference is made to the information given above.

The present invention accordingly provides the process as described above in which the belt calciner has precisely one heating zone and an inert gas $I_1$, preferably nitrogen, flows through the support to be heated according to b) in the heating zone, where $I_1$ preferably comprises less than 10 ppm, more preferably from 5 to 9 ppm, of oxygen, $I_1$ preferably has a temperature in the range from $T_1$ to $1.1\,T_1$, more preferably from $T_1$ to $1.07\,T_1$, more preferably from $T_1$ to $1.05\,T_1$ and $I_1$ preferably flows through the support at a volume flow in the range from 2500 to 5000 m$^3$/h, more preferably from 3200 to 4500 m$^3$/h.

In a particularly preferred embodiment of the present invention, the gas stream introduced into the heating zone is heated in a suitable way to the temperature in the range from $T_1$ to $1.1\,T_1$, more preferably in the range from $T_1$ to $1.07\,T_1$, more preferably in the range from $T_1$ to $1.05\,T_1$, before introduction.

The present invention further provides the process as described above in which the belt calciner has precisely one hold zone following the heating zone, where the support which has been heated to $T_1$ is maintained at a temperature $T_2$ in the hold zone and an inert gas $I_2$, preferably nitrogen, flows through the support being maintained at the temperature $T_2$ in the hold zone, $I_2$ preferably comprises less than 10 ppm, more preferably from 5 to 9 ppm, of oxygen, $I_2$ preferably has a temperature in the range from $T_2$ to $1.05\,T_2$ and $I_2$ preferably flows through the support at a volume flow in the range from 1000 to 3000 m$^3$/h, more preferably from 1500 to 2000 m$^3$/h.

In a particularly preferred embodiment of the present invention, the gas stream introduced into the hold zone is heated in a suitable way to the temperature in the range from $T_2$ to $1.1\,T_2$, more preferably in the range from $T_2$ to $1.07\,T_2$, more preferably in the range from $T_2$ to $1.05\,T_2$, for example in the range from $T_2$ to $1.04\,T_2$ or in the range from $T_2$ to $1.03\,T_2$ or in the range from $T_2$ to $1.02\,T_2$ or in the range from $T_2$ to $1.01\,T_2$, before introduction.

According to the present invention, the preferred belt calciner can have, in addition to the at least one, preferably precisely one, heating zone and the at least one, preferably precisely one, hold zone, at least one cooling zone for carrying out step d) which is particularly preferably provided in the belt calciner immediately after the hold zone or the last of the hold zones.

As regards the preferred parameters for the cooling according to step d), reference is made to the information given above.

The present invention therefore also provides the process as described above in which the belt calciner has a cooling zone following the hold zone and cooling of the support maintained at the temperature $T_2$ to a temperature $T_3$, preferably not more than 60° C., is carried out in the cooling zone.

The present invention likewise provides the process as described above in which the belt calciner has a cooling zone following the hold zone and cooling of the support maintained at the temperature $T_2$ to a temperature $T_3$, preferably not more than 60° C., is carried out in the cooling zone and cooling according to d) is carried out in an atmosphere comprising at least 15% by volume of oxygen.

For the purposes of the present invention, either at least one of the heating zones, preferably the precisely one heating zone, and/or at least one of the hold zones, preferably the precisely one hold zone, and/or at least one of the cooling zones, preferably the precisely one cooling zone, can have a pressure which is increased or reduced compared to ambient pressure. Should one of these zones have a pressure lower than ambient pressure, the pressure is, for example, up to 10 mbar, preferably up to 5 mbar, lower than ambient pressure. Should one of these zones have a pressure higher than ambient pressure, the pressure is, for example, up to 10 mbar, preferably up to 5 mbar, higher than ambient pressure.

In a preferred embodiment of the belt calciner which is preferably used in the process of the invention, the gas stream, preferably the stream of inert gas $I_1$ is conveyed in a single pass through the heating zone and the gas stream is more preferably passed from the top downward through the heating zone. The term "single pass" as used in the present context refers to a mode of operation in which the gas stream is introduced into the heating zone and conveyed, essentially without mixing, over the support and then discharged essentially without mixing from the heating zone and it is additionally ensured that, after contact of a given volume element of the gas stream with the support, this volume element no longer comes into contact with the support. In the context of the present invention, it has been found that such a single pass is advantageous for achieving the high heating rates according to the invention of at least 30 K/min. To ensure such a single pass, it has also been found to be advantageous not to use apparatuses such as fans which are usually provided in belt calciners and by means of which the gas atmosphere is circulated in the individual zones.

Furthermore, in a preferred embodiment of the belt calciner which is preferably used according to the invention in the process of the invention, the gas stream, preferably the stream of inert gas $I_2$, is conveyed in a single pass through the hold zone and the gas stream is more preferably conveyed from the top downward through the hold zone.

The present invention therefore provides the process as described above in which at least the inert gas $I_1$ is conveyed in a single pass through the heating zone, with preference being given to the inert gas $I_1$ being conveyed in a single pass through the heating zone and the inert gas $I_2$ being conveyed in a single pass through the hold zone.

The gas stream, preferably the stream of the inert gas $I_1$, which is discharged from the heating zone after the single pass through the heating zone and preferably likewise the gas stream, preferably the stream of the inert gas $I_2$, which is discharged from the hold zone after the single pass through the hold zone can be conveyed separately from one another or appropriately combined to a suitable use. For example, it is possible to purify the gas streams in an appropriate way and then reuse them in the process of the invention. In the process of the invention, the gas streams are particularly preferably not recirculated to the process. In this case in which no recirculation is carried out, the gas streams are preferably fed to a purification stage in which the amines introduced into the gas stream in the calcination are preferably removed from the gas streams. One possible purification according to the invention is, for example, an acidic scrubbing of the gas streams, which can be carried out, for example, in one or more scrubbing columns. As acidic scrubbing medium, it is possible to employ, for example, an aqueous sulfuric acid solution. The present invention therefore also provides the process as described above in which at least the inert gas $I_1$, preferably the inert gases $I_1$ and $I_2$, are not recirculated to the heating zone and/or the hold zone of the belt calciner.

The present invention therefore also provides the process as described above in which the belt calciner comprises:
(i) precisely one heating zone having a device for introducing a gas stream into the heating zone and a device for discharging the gas stream from the heating zone;
(ii) precisely one hold zone which directly follows the heating zone and has a device for introducing a gas stream into the hold zone and a device for discharging the gas stream from the hold zone; and
(iii) optionally precisely one cooling zone which directly follows the hold zone and has a device for introducing a gas stream into the cooling zone and a device for discharging the gas stream from the cooling zone;
where the belt calciner does not have a device for circulating the gas stream introduced into the heating zone in the heating zone and does not have a device for circulating the gas stream introduced into the hold zone in the hold zone and the belt calciner does not have a device for recirculating the gas streams discharged from the heating zone and from the hold zone.

The present invention likewise provides a belt calciner for use in a process for producing a catalyst for the oxidation of ethylene to ethylene oxide, which comprises
(i) precisely one heating zone having a device for introducing a gas stream into the heating zone and a device for discharging the gas stream from the heating zone;
(ii) precisely one hold zone which directly follows the heating zone and has a device for introducing a gas stream into the hold zone and a device for discharging the gas stream from the hold zone; and
(iii) optionally precisely one cooling zone which directly follows the hold zone and has a device for introducing a gas stream into the cooling zone and a device for discharging the gas stream from the cooling zone;
where the belt calciner does not have a device for circulating the gas stream introduced into the heating zone in the heating zone and does not have a device for circulating the gas stream introduced into the hold zone in the hold zone and the belt calciner does not have a device for recirculating the gas streams discharged from the heating zone and from the hold zone.

For the purposes of the present invention, the belt calciner can be configured so that at least the housing surrounding the heating zone is heatable. It is also possible for the housing surrounding the heating zone to be able to be heated to a temperature which is sufficient for the high heating rate according to the invention in step b) not to be adversely affected. Furthermore, it is possible for the housing surrounding the heating zone to be able to be heated to a temperature $T_1$, as described above, particularly preferably to a temperature $T_1$ in the range from 250 to 295° C.

For the purposes of the present invention, the belt calciner can also be configured so that the housing surrounding the hold zone is also heatable. It is also possible for the housing surrounding the hold zone to be able to be heated to a temperature which is sufficient for the hold temperature $T_2$ employed according to the invention in step c) not to be adversely affected. Furthermore, it is possible for the housing surrounding the hold zone to be able to be heated to a temperature $T_2$, as described above, particularly preferably to a temperature $T_2$ in the range from $T_1$ to $1.05\,T_1$.

In a preferred embodiment of the present invention, the belt calciner is configured so that a housing which directly surrounds a zone is not heatable. In this case, particular preference is given to providing a housing which encloses the individual housings directly surrounding the heating zone and the hold zone, with this outer housing being heatable. Here, further preference is given to carrying out the calcination according to the invention in such a way that the housing is appropriately heated during the ongoing calcination and has a temperature of at least 130° C. As regards the individual housings directly surrounding the heating zone and the hold zone, these are preferably insulated in an appropriate way.

As described above, preference is given according to the invention to the gas introduced into the heating zone, in particular the inert gas $I_1$, being heated in an appropriate way before introduction. As described above, further preference is given according to the invention to the gas introduced into the hold zone, particularly preferably the inert gas $I_2$, being heated in an appropriate way before introduction.

As also described above, the support is provided at a temperature $T_0$ in step a), where the temperature $T_0$ is preferably in the range from 5 to 20° C., more preferably in the range from 5 to 15° C. In the preferred embodiment of the process of the invention in which the belt calciner as described above is used, particular preference is given to introducing the support to be calcined into the heating zone by means of a coolable feed device. For example, a coolable chute or a coolable conveyor belt is preferred. This coolable feed device can preferably be cooled to the temperature $T_0$.

In the provision as per a), it can be necessary for the support obtained after the impregnation not to be passed immediately to the heating according to b) but instead to be stored for a particular time. In this case, the support after the impregnation is preferably cooled during storage for this time, with the preferred temperature at which the impregnated support is stored preferably being in the range from 5 to 20° C., more preferably in the range from 5 to 15° C. The support which has been cooled during storage in this way is preferably passed by means of the above-described cooled feed device to the heating according to b).

According to the invention, it has also been found that the support, which is to be heated to the temperature $T_1$ and preferably maintained at the temperature $T_2$ in the belt calciner, preferably used according to the invention, is preferably conveyed essentially in a monolayer through the belt calciner on the belt running through the belt calciner. According to the invention, it is therefore preferably ensured, by means of a suitable measure, that essentially only a single layer of the support is present on the belt of the belt calciner, so that the shaped support bodies do not rest on top of one another but essentially side by side.

As regards the belt calciner, particular preference is given, according to the invention, to the embodiments described below and the combinations of embodiments given by the back-references described below:

1. A belt calciner, in particular for use in a process for producing a catalyst for the oxidation of ethylene to ethylene oxide, which comprises
   (i) precisely one heating zone having a device for introducing a gas stream into the heating zone and a device for discharging the gas stream from the heating zone;
   (ii) precisely one hold zone which directly follows the heating zone and has a device for introducing a gas stream into the hold zone and a device for discharging the gas stream from the hold zone; and
   (iii) optionally precisely one cooling zone which directly follows the hold zone and has a device for introducing a gas stream into the cooling zone and a device for discharging the gas stream from the cooling zone;
   where the belt calciner does not have a device for circulating the gas stream introduced into the heating zone in the heating zone and does not have a device for circulating the gas stream introduced into the hold zone in the hold zone and the belt calciner does not have a device for recirculating the gas streams discharged from the heating zone and from the hold zone.

2. The belt calciner according to embodiment 1, which comprises a housing surrounding the heating zone, a housing surrounding the hold zone and a housing surrounding both the housing surrounding the heating zone and the housing surrounding the hold zone, where the housing surrounding both the housing surrounding the heating zone and the housing surrounding the hold zone is heatable, preferably electrically heatable.

3. The belt calciner according to embodiment 2, wherein the housing surrounding both the housing surrounding the heating zone and the housing surrounding the hold zone can be heated to a temperature of at least 130° C., preferably electrically.

4. The belt calciner according to any of embodiments 1 to 3, which comprises a device which is located upstream of the heating zone and serves to heat the gas stream to be introduced into the heating zone, preferably to heat the gas stream to be introduced into the heating zone to a temperature in the range from $T_1$ to $1.1\,T_1$, more preferably in the range from $T_1$ to $1.07\,T_1$, more preferably in the range from $T_1$ to $1.05\,T_1$.

5. The belt calciner according to any of embodiments 1 to 4, which comprises a device which is located upstream of the hold zone and serves to heat the gas stream to be introduced into the hold zone, preferably to heat the gas stream to be introduced into the hold zone to a temperature in the range from $T_2$ to $1.1\,T_2$, more preferably in the range from $T_2$ to $1.07\,T_2$, more preferably in the range from $T_2$ to $1.05\,T_2$, for example in the range from $T_2$ to $1.04\,T_2$ or in the range from $T_2$ to $1.03\,T_2$ or in the range from $T_2$ to $1.02\,T_2$ or in the range from $T_2$ to $1.01\,T_2$.

6. The belt calciner according to any of embodiments 1 to 5, which comprises a feed device which can be cooled to a temperature $T_0$ in the range from 5 to 20° C. and serves to feed the catalyst to be calcined into the heating zone.

7. The belt calciner according to any of embodiments 1 to 6, which comprises a storage facility which can be cooled to a temperature $T_0$ in the range from 5 to 20° C. and serves to cool and store the catalyst to be calcined.

8. The belt calciner according to embodiment 7, wherein the feed device according to claim 6 is connected in a suitable way to the storage facility according to claim 7 for accommodating the stored support.

9. The use of a belt calciner according to any of claims 1 to 8 in a process for producing a catalyst for the oxidation of ethylene to ethylene oxide.

It has surprisingly been found that the support which has been heated at the high heating rate according to the invention in step a) in the belt calciner as described above, in particular the support which has been heated in the inert gas atmosphere as described above in the belt calciner as described above, has advantageous properties as catalyst in the oxidation of ethylene to ethylene oxide.

The present invention therefore also provides a catalyst for the oxidation of ethylene to ethylene oxide which is obtainable or obtained by a process as described above.

The present invention likewise provides a process for preparing ethylene oxide by gas-phase oxidation of ethylene by means of molecular oxygen in a fixed-bed reactor in the presence of this catalyst.

Process for Preparing Ethylene Oxide

According to the invention, the oxidation of ethylene to ethylene oxide can be carried out by all processes known to those skilled in the art. It is possible to use all reactors which can be used in the ethylene oxide production processes of the prior art, for example externally cooled shell-and-tube reactors or reactors having a loose catalyst bed and cooling tubes. The oxidation is preferably carried out in a tube reactor, preferably in a shell-and-tube reactor.

As regards the reaction conditions, reference may be made by way of example to the relevant disclosure in DE 25 21 906 A1, EP 0 014 457 A2, DE 2 300 512 A1, EP 0 172 565 A2, DE 24 54 972 A1, EP 0 357 293 A1, EP 0 266 015 A1, EP 0 085 237 A1, EP 0 082 609 A1 and EP 0 339 748 A2. In principle, inert gases such as nitrogen or gases which are inert under the reaction conditions, e.g. steam, methane, and optionally reaction moderators such as halides, hydrocarbons such as ethyl chloride, vinyl chloride or 1,2-dichloroethane can additionally be mixed into the reaction gas comprising ethane and oxygen. The oxygen content in the reactor is advantageously in a range at which no explosive gas mixture is formed.

The above-described constituents of the reaction mixture may have small amounts of impurities. Ethylene can, for example, be used in any degree of purity suitable for the gas-phase oxidation according to the invention. Suitable degrees of purity of ethylene are, for example, "polymer-grade" ethylene which typically has a purity of at least 99% or "chemical-grade" ethylene which typically has a purity of 95% or less. The impurities typically comprise, in particular, ethane, propane and/or propene.

The oxidation of ethylene to ethylene oxide is usually carried out at elevated temperature. Preference is given to temperatures in the range from 150 to 350° C., more preferably in the range from 180 to 300° C., more preferably temperatures in the range from 190° C. to 280° C. and particularly preferably temperatures in the range from 200° C. to 280° C.

The oxidation of ethylene to ethylene oxide is preferably carried out at pressures in the range from 5 to 30 bar. The oxidation is more preferably carried out at a pressure in the range from 5 bar to 25 bar, more preferably at a pressure in the range from 10 bar to 20 bar and in particular in the range from 14 bar to 20 bar.

The oxidation is preferably carried out in a continuous process. If the reaction is carried out continuously, the GHSV (gas hourly space velocity) is, depending on the type of reactor chosen, for example on the size/cross-sectional area of the reactor, the shape and size of the catalyst, preferably in the range from 800/h to 10000/h, preferably in the range from 2000/h to 6000/h, more preferably in the range from 2500/h to 5000/h, in each case based on the volume of the catalyst bed in the reactor.

The preparation of ethylene oxide from ethylene and oxygen can be carried out in a recycle process. Here, the reaction mixture is circulated through the reactor with the newly formed ethylene oxide and also the by-products formed in the reaction being removed from the product stream after each pass and the product stream being, after having been supplemented with the required amounts of, for example, ethylene, oxygen and/or reaction moderators, reintroduced into the reactor.

The separation of the ethylene oxide from the product stream and any subsequent optional work-up can be carried out by customary methods of the prior art (cf. Ullmann's Encyclopedia of Industrial Chemistry, 5th edition, vol. A-10, pp. 117-135, in particular 123-125, VCH-Verlagsgesellschaft, Weinheim 1987).

Preferred processes and catalysts of the invention are described in the embodiments 1 to 22 below and the combinations of embodiments given by the respective back-references. As regards preferred embodiments which relate to the configuration of the belt calcination described below, reference may be made to the above-described preferred embodiments 1 to 8 which are incorporated by reference into the preferred embodiments 1 to 22 described below and are therefore to be read together with the embodiments 1 to 22.

1. A process for producing a catalyst for the oxidation of ethylene to ethylene oxide, which comprises
   a) impregnating a support comprising alumina with an aqueous solution comprising a silver-comprising compound and providing the impregnated support at a temperature $T_0$;
   b) heating the impregnated support from the temperature $T_0$ to a temperature $T_1$ at a heating rate of at least 30 K/min.
2. The process according to embodiment 1, wherein the heating rate is in the range from 30 to 80 K/min, preferably in the range from 40 to 75 K/min.
3. The process according to embodiment 1 or 2, wherein the temperature $T_0$ is in the range from 5 to 20° C., preferably in the range from 10 to 15° C.
4. The process according to any of embodiments 1 to 3, wherein the temperature $T_1$ is in the range from 250 to 295° C., preferably in the range from 270 to 290° C.
5. The process according to any of embodiments 1 to 4, wherein the heating according to b) is effected by bringing the support into contact with an inert gas $I_1$, preferably with nitrogen, where $I_1$ preferably comprises less than 10 ppm, more preferably from 5 to 9 ppm, of oxygen.
6. The process according to embodiment 5, wherein $I_1$ has a temperature in the range from $T_1$ to 1.1 $T_1$.
7. The process according to any of embodiments 1 to 6, which further comprises
   c) maintaining the support which has been heated to the temperature $T_1$ at a temperature $T_2$ which is preferably in the range from 0.90 $T_1$ to 1.1 $T_1$.
8. The process according to embodiment 7, wherein the support is maintained at the temperature $T_2$ according to c) by means of an inert gas $I_2$, preferably by means of nitrogen, where the inert gas $I_2$ preferably comprises less than 10 ppm, more preferably from 5 to 9 ppm, of oxygen and the inert gas preferably has a temperature in the range from $T_2$ to 1.05 $T_2$.
9. The process according to embodiment 7 or 8, wherein the support is maintained at the temperature $T_2$ for a time in the range from 1 to 15 minutes, preferably from 2 to 10 minutes, more preferably from 3 to 5 minutes, in c).
10. The process according to any of embodiments 1 to 9, which further comprises d) cooling the support which has been maintained at the temperature $T_2$ to a temperature $T_3$ which is not more than 60° C.
11. The process according to embodiment 10, wherein the cooling according to d) is carried out in an atmosphere comprising at least 5% by volume, preferably at least 15% by volume, of oxygen, more preferably in air.
12. The process according to any of embodiments 1 to 11, wherein at least the heating according to b) is carried out in a belt calciner.
13. The process according to embodiment 12, wherein the belt calciner has precisely one heating zone and an inert gas $I_1$, preferably nitrogen, flows through the support to be heated according to b) in the heating zone, where $I_1$ preferably comprises less than 10 ppm, more preferably from 5 to 9 ppm, of oxygen, $I_1$ preferably has a temperature in the range from $T_1$ to $1.1\ T_1$, and $I_1$ preferably flows through the support at a volume flow in the range from 2500 to 5000 m³/h, more preferably from 3200 to 4500 m³/h.
14. The process according to embodiment 12 or 13, wherein the belt calciner has precisely one hold zone following the heating zone, where the support which has been heated to $T_1$ is maintained at a temperature $T_2$ in the hold zone and an inert gas $I_2$, preferably nitrogen, flows through the support being maintained at the temperature $T_2$ in the hold zone, $I_2$ preferably comprises less than 10 ppm, more preferably from 5 to 9 ppm, of oxygen, $I_2$ preferably has a temperature $T_2$, and $I_2$ preferably flows through the support at a volume flow in the range from 1000 to 3000 m³/h, more preferably from 1500 to 2000 m³/h.
15. The process according to embodiment 14, wherein the belt calciner has a cooling zone following the hold zone, and cooling of the support maintained at the temperature $T_2$ to a temperature $T_3$, preferably not more than 60° C., is carried out in the cooling zone.
16. The process according to embodiment 14 or 15, wherein at least the inert gas $I_1$ is conveyed in a single pass through the heating zone, with preference being given to the inert gas $I_1$ being conveyed in a single pass through the heating zone and the inert gas $I_2$ being conveyed in a single pass through the hold zone.
17. The process according to any of embodiments 14 to 16, wherein at least the inert gas $I_1$, preferably the inert gases $I_1$ and $I_2$ are not recirculated to the heating zone and/or the hold zone of the belt calciner.
18. The process according to any of embodiments 1 to 17, wherein the support comprising alumina is additionally impregnated with rhenium or with a rhenium-comprising compound, preferably also additionally with tungsten or with a tungsten-comprising compound and/or with lithium or with a lithium-comprising compound and/or with cesium or with a cesium-comprising compound and the support is optionally impregnated with sulfur or with a sulfur-comprising compound in a).
19. The process according to embodiment 18, wherein the aqueous solution comprising a silver-comprising compound used in a) additionally comprises a rhenium-comprising compound, preferably additionally a tungsten-comprising compound and/or a lithium-comprising compound and/or a cesium-comprising compound and optionally a sulfur-comprising compound.
20. The process according to any of embodiments 1 to 19, wherein the support comprising alumina which is provided according to a) has a cylindrical geometry, where the cylinder preferably has a length in the range from 5 to 10 mm, an external diameter in the range from 5 to 10 mm and a ratio of external diameter in mm to wall thickness in mm in the range from 2.5 to 4.5.
21. A catalyst for the oxidation of ethylene to ethylene oxide which is obtainable or obtained by a process according to any of embodiments 1 to 20.
22. A process for preparing ethylene oxide by gas-phase oxidation of ethylene by means of molecular oxygen in a fixed-bed reactor in the presence of a catalyst according to embodiment 21.

Particularly preferred embodiments of the invention are indicated below, including the embodiments resulting from the combinations given by the back-references being explicitly:
1. A process for producing a catalyst for the oxidation of ethylene to ethylene oxide, which comprises
   a) impregnating a support comprising alumina with an aqueous solution comprising a silver-comprising compound and providing the impregnated support at a temperature $T_0$;
   b) heating the impregnated support from the temperature $T_0$ to a temperature $T_1$ at a heating rate of at least 30 K/min.
2. The process according to embodiment 1, wherein the heating rate is in the range from 30 to 80 K/min, preferably in the range from 40 to 75 K/min.
3. The process according to embodiment 1 or 2, wherein the temperature $T_0$ is in the range from 5 to 20° C., preferably in the range from 10 to 15° C.
4. The process according to any of embodiments 1 to 3, wherein the temperature $T_1$ is in the range from 250 to 295° C., preferably in the range from 270 to 290° C.
5. The process according to any of embodiments 1 to 4, wherein the heating according to b) is effected by bringing the support into contact with an inert gas $I_1$, preferably with nitrogen, where $I_1$ preferably comprises less than 10 ppm, more preferably from 5 to 9 ppm, of oxygen.
6. The process according to embodiment 5, wherein $I_1$ has a temperature in the range from $T_1$ to $1.1\ T_1$.
7. The process according to any of embodiments 1 to 6, which further comprises
   c) maintaining the support which has been heated to the temperature $T_1$ at a temperature $T_2$ which is preferably in the range from $0.90\ T_1$ to $1.1\ T_1$.
8. The process according to embodiment 7, wherein the support is maintained at the temperature $T_2$ according to c) by means of an inert gas $I_2$, preferably by means of nitrogen, where the inert gas $I_2$ preferably comprises less than 10 ppm, more preferably from 5 to 9 ppm, of oxygen and the inert gas preferably has a temperature in the range from $T_2$ to $1.05\ T_2$.
9. The process according to embodiment 7 or 8, wherein the support is maintained at the temperature $T_2$ for a time in the range from 1 to 15 minutes, preferably from 2 to 10 minutes, more preferably from 3 to 5 minutes, in c).
10. The process according to any of embodiments 1 to 9, which further comprises
    d) cooling the support which has been maintained at the temperature $T_2$ to a temperature $T_3$ which is not more than 60° C.
11. The process according to embodiment 10, wherein the cooling according to d) is carried out in an atmosphere comprising at least 5% by volume, preferably at least 15% by volume, of oxygen, more preferably in air.
12. The process according to any of embodiments 1 to 11, wherein the support comprising alumina is additionally impregnated with rhenium or with a rhenium-comprising compound, preferably also additionally with tungsten or with a tungsten-comprising compound and/or with lithium or with a lithium-comprising compound and/or with cesium or with a cesium-comprising compound and the support is optionally impregnated with sulfur or with a sulfur-comprising compound in a).

13. The process according to embodiment 12, wherein the aqueous solution comprising a silver-comprising compound used in a) additionally comprises a rhenium-comprising compound, preferably additionally a tungsten-comprising compound and/or a lithium-comprising compound and/or a cesium-comprising compound and optionally a sulfur-comprising compound.

14. The process according to any of embodiments 1 to 13, wherein the support comprising alumina which is provided according to a) has a cylindrical geometry, where the cylinder preferably has a length in the range from 5 to 10 mm, an external diameter in the range from 5 to 10 mm and a ratio of external diameter in mm to wall thickness in mm in the range from 2.5 to 4.5.

15. A catalyst for the oxidation of ethylene to ethylene oxide obtainable or obtained by a process according to any of embodiments 1 to 14.

16. A process for preparing ethylene oxide by gas-phase oxidation of ethylene by means of molecular oxygen in a fixed-bed reactor in the presence of a catalyst according to embodiment 15.

The present invention is illustrated by the following examples and comparative examples:

EXAMPLES

Reference Example 1

Production of an Impregnated Support 1.1

TABLE 1a

Chemical and physical properties of the alumina support used according to the invention (Examples 1-5) having a bimodal pore distribution

| | |
|---|---|
| Ca | 600 |
| K | 200 |
| Mg | 100 |
| Na | 200 |
| Si | 500 |
| Zr | <100 |
| Ti | <100 |
| Zn | <100 |
| Fe | 100 |
| Water uptake [ml/g] | 0.441 |
| BET surface area [m$^2$/g] | 0.65 |
| Peak maxima of the pore diameters, determined by Hg porosimetry [microns] | 1.3 and 60.9 |
| Geometry: external diameter × length × internal diameter (in mm) | 6.04 × 5.55 × 2.43 |

TABLE 1b

Chemical and physical properties of the alumina support used according to the invention (Example 6) having a bimodal pore distribution

| | |
|---|---|
| Ca | 800 |
| K | 100 |
| Mg | 200 |
| Na | 400 |

TABLE 1b-continued

Chemical and physical properties of the alumina support used according to the invention (Example 6) having a bimodal pore distribution

| | |
|---|---|
| Si | 800 |
| Zr | <100 |
| Ti | <100 |
| Zn | <100 |
| Fe | 100 |
| Water uptake [ml/g] | 0.484 |
| BET surface area [m$^2$/g] | 0.78 |
| Peak maxima of the pore diameters, determined by Hg porosimetry [microns] | 1.27 and 61.0 |
| Geometry: external diameter × length × internal diameter (in mm) | 6.03 × 5.59 × 2.35 |

1.2 Production of the Silver Complex Solution 1.5 l of deionized water were placed in a vessel and 550 g of silver nitrate were added while stirring and completely dissolved therein. The solution was heated to 40° C. during this procedure. 402.62 g of potassium hydroxide solution (47.8%) were mixed with 1.29 l of deionized water. 216.31 g of oxalic acid were subsequently added and completely dissolved and the solution was heated to 40° C. The potassium oxalate solution was subsequently added to the silver nitrate solution (40° C.) by means of a metering pump over a period of about 45 minutes (volume flow=about 33 ml/min). After the addition was complete, the solution obtained was stirred at 40° C. for a further 1 hour. The precipitated silver oxalate was filtered off and the filter cake obtained was washed with 1 l portions of water (about 10 l) until it was free of potassium and nitrate (determined by means of conductivity measurements on the washings; for the present purposes, free of potassium and nitrate means a conductivity of <40 μS/cm). The water was removed from the filter cake as completely as possible and the residual moisture content of the filter cake was determined. 620 g of silver oxalate having a water content of 20.80% were obtained. 306 g of ethylenediamine were cooled to about 10° C. by means of an ice bath and 245 g of water were added in small portions. After the addition of water was complete, 484.7 g of the (still moist) silver oxalate obtained were added in small portions over a period of about 30 minutes. The mixture was stirred overnight at room temperature and the residue was subsequently centrifuged off. The Ag content of the remaining clear solution was determined by refractometry and the density was determined by means of a 10 ml measuring cylinder.

The solution obtained comprised 29.14% by weight of silver, calculated as element, and had a density of 1.532 g/ml.

1.3 General Production of the Solution Comprising Silver and Promoters 97.1004 g of the silver complex solution were placed in a vessel. 1.1047 g of an aqueous solution of lithium and sulfur (2.85% by weight of lithium from lithium nitrate and 0.21% by weight of sulfur from ammonium sulfate), 1.791 g of an aqueous solution of tungsten and cesium (2% by weight of tungsten from tungstic acid and 3.5% by weight of cesium from cesium hydroxide 50% in H$_2$O) and 1.6492 g of an aqueous solution of rhenium (3.1% by weight ammonium perrhenate) were added thereto and the solution was stirred for 5 minutes.

1.4 General Method of Applying the Solution to the Support 140.61 g of the support (see Table 1) were placed in a rotary evaporator and evacuated. The vacuum was 20 mbar. The support was preevacuated for about 10 minutes. The solution obtained according to method 1.3 was dripped onto the support over a period of 15 minutes and the impregnated support was subsequently allowed to rotate for a further 15 minutes under reduced pressure. The support was then left to stand in the apparatus at room temperature and atmospheric pressure for 1 hour and gently mixed every 15 minutes.

1.5 General Production of Crushed Catalyst

The catalyst rings obtained were roughly crushed by means of a mortar in a porcelain dish. The broken up material was subsequently brought to the desired particle size fraction (500-900 µm) by means of a sieving machine, round sieve and balls. Very hard rings were completely broken up by means of the mortar and then sieved.

1.6 General Method of Testing the Catalysts (Epoxidation of Ethylene)

The epoxidations were carried out in an experimental reactor comprising an upright stainless steel reaction tube having an internal diameter of 6 mm and a length of 2200 mm. The reaction tube provided with a jacket was heated by means of hot oil having the temperature T(oil) which flowed through the jacket. To a very good approximation, the temperature of the oil corresponds to the temperature in the reaction tube and thus the reaction temperature. The reaction tube was filled from the bottom upward to a height of 212 mm with inert steatite spheres (1.0-1.6 mm), then to a height of 1100 mm with 38.2 g of crushed catalyst, particle size 0.5-0.9 mm, and then to a height of 707 mm with inert steatite spheres (1.0-1.6 mm). The feed gas entered the reactor from the top and left it again at the lower end after passing through the catalyst bed. The feed gas comprised 35% by volume of ethylene, 7% by volume of oxygen, 1% by volume of $CO_2$. At the beginning, 2.5 ppm of EC (ethylene chloride) were used for start-up. Depending on the catalyst and performance, the EC concentration was increased every 24 hours to a maximum of 8 ppm. The remainder of the feed gas was methane. The experiments were carried out at a pressure of 15 bar and a space velocity of gas (GHSV) of 4750/h and a space-time yield of 250 kg of EO (ethylene oxide)/($m^3$(cat)×h). The reaction temperature was regulated to maintain the prescribed ethylene oxide offgas concentration of 2.7%. To optimize the catalyst in respect of selectivity and conversion, from 2.2 to 8.0 ppm of ethylene chloride were added as moderator to the feed gas. The gas leaving the reactor was analyzed by means of on-line MS. The selectivity was determined from the analytical results.

Example 1

According to the Invention 360.1 g of the support as per Table 1a (see 1.1 above) were treated according to the general method 1.4 with 237.3 g of the impregnation solution. The vacuum cold water uptake of the alumina support was used to calculate the amounts required for producing the catalyst according to 1.4.

The following amounts were used in the production of the solution according to the general method 1.4:
226.97 g of silver complex solution (29.14% of Ag, density 1.528 g/ml)
2.8446 g of a solution comprising 2.85% of lithium and 0.21% of sulfur,
4.2669 g of a solution comprising 2.00% of tungsten and 3.5% of cesium,
3.2262 g of a solution comprising 4.1% of rhenium.

130 g of the moist catalyst obtained according to the general method 1.4 were subsequently calcined under the following conditions: oven temperature 283° C., nitrogen flow 8.3 $m^3$/h, heating rate 32 K/min, heating time 450 s to an internal catalyst temperature of 265° C., hold time at 265° C. 390 s, cooling to room temperature over a period of 420 s. The catalyst obtained was subsequently tested according to the general method 1.6. The result is shown in Table 2.

Example 2

According to the Invention 100.1 g of the support as per Table 1a (see 1.1 above) were treated according to the general method 1.4 with 65.89 g of the impregnation solution. The vacuum cold water uptake of the alumina support was used to calculate the amounts required for producing the catalyst according to 1.4.

The following amounts were used in the production of the solution according to the general method 1.4:
62.64 g of silver complex solution (29.35% of Ag, density 1.532 g/ml)
0.7907 g of a solution comprising 2.85% of lithium and 0.21% of sulfur,
1.1861 g of a solution comprising 2.00% of tungsten and 3.5% of cesium,
0.8968 g of a solution comprising 4.1% of rhenium,
0.3830 g of water.

100 g of the moist catalyst obtained according to the general method 1.4 were subsequently calcined under the following conditions: oven temperature 283° C., nitrogen flow 8.3 $m^3$/h, heating rate 40 K/min, heating time 360 s to an internal catalyst temperature of 266° C., hold time at 266° C. 360 s, cooling to room temperature over a period of 420 s. The catalyst obtained was subsequently tested according to the general method 1.6. The result is shown in Table 2.

Example 3

According to the Invention 330 g of the support as per Table 1a (see 1.1 above) were treated according to the general method 1.4 with 217.4 g of the impregnation solution. The vacuum cold water uptake of the alumina support was used to calculate the amounts required for producing the catalyst according to 1.4.

The following amounts were used in the production of the solution according to the general method 1.4:
205.1 g of silver complex solution (29.35% of Ag, density 1.539 g/ml)
2.6041 g of a solution comprising 2.85% of lithium and 0.21% of sulfur,
3.9061 g of a solution comprising 2.00% of tungsten and 3.5% of cesium,
3.9061 g of a solution comprising 3.1% of rhenium,
1.8545 g of water.

63.9 g of the moist catalyst obtained according to the general method 1.4 were subsequently calcined under the following conditions: oven temperature 283° C., nitrogen flow 8.3 $m^3$/h, heating rate 67 K/min, heating time 185 s to an internal catalyst temperature of 260° C., hold time at 262° C. 415 s, cooling to room temperature over a period of 420 s. The catalyst obtained was subsequently tested according to the general method 1.6. The result is shown in Table 2.

Example 4

Comparative Example 350.1 g of the support as per Table 1a (see 1.1 above) were treated according to the general method 1.4 with 230.5 g of the impregnation solution. The vacuum cold water uptake of the alumina support was used to calculate the amounts required for producing the catalyst according to 1.4.

The following amounts were used in the production of the solution according to the general method 1.4:
219.08 g of silver complex solution (29.35% of Ag, density 1.532 g/ml)
2.7656 g of a solution comprising 2.85% of lithium and 0.21% of sulfur,
4.1484 g of a solution comprising 2.00% of tungsten and 3.5% of cesium,
3.1366 g of a solution comprising 4.1% of rhenium,
1.3397 g of water.

350 g of the moist catalyst obtained according to the general method 1.4 were subsequently calcined under the following conditions: oven temperature 283° C., nitrogen flow 8.3 m³/h, heating rate 19 K/min, heating time 780 s to an internal catalyst temperature of 266° C., hold time at 266° C. 720 s, cooling to room temperature over a period of 420 s. The catalyst obtained was subsequently tested according to the general method 1.6. The result is shown in Table 2.

Example 5

Comparative Example 360.1 g of the support as per Table 1a (see 1.1 above) were treated according to the general method 1.4 with 237.3 g of the impregnation solution. The vacuum cold water uptake of the alumina support was used to calculate the amounts required for producing the catalyst according to 1.4.

The following amounts were used in the production of the solution according to the general method 1.4:
226.97 g of silver complex solution (29.14% of Ag, density 1.528 g/ml)
2.8446 g of a solution comprising 2.85% of lithium and 0.21% of sulfur,
4.2669 g of a solution comprising 2.00% of tungsten and 3.5% of cesium,
3.2262 g of a solution comprising 4.1% of rhenium.

160 g of the moist catalyst obtained according to the general method 1.4 were subsequently calcined under the following conditions: oven temperature 283° C., nitrogen flow 8.3 m³/h, heating rate 28 K/min, heating time 510 s to an internal catalyst temperature of 264° C., hold time at 264° C. 330 s, cooling to room temperature over a period of 420 s. The catalyst obtained was subsequently tested according to the general method 1.6. The result is shown in Table 2.

Example 6

Comparative Example 400 g of the support as per Table 1b (see 1.1 above) were treated according to the general method 1.4 with 281.36 g of the impregnation solution. The vacuum cold water uptake of the alumina support was used to calculate the amounts required for producing the catalyst according to 1.4.

The following amounts were used in the production of the solution according to the general method 1.4:
253.96 g of silver complex solution (29.35% of Ag, density 1.532 g/ml)
3.1600 g of a solution comprising 2.85% of lithium and 0.21% of sulfur,
4.7400 g of a solution comprising 2.00% of tungsten and 4.0% of cesium,
4.7400 g of a solution comprising 3.1% of rhenium,
14.7581 g of water.

400 g of the moist catalyst obtained according to the general method 1.4 were subsequently calcined under the following conditions: oven temperature 289° C., nitrogen flow 1.0 m³/h, heating rate 26 K/min, heating time 600 s to an internal catalyst temperature of 289° C., hold time at 280° C. 1800 s, cooling to room temperature over a period of 420 s. The catalyst obtained was subsequently tested according to the general method 1.6. The result is shown in Table 2.

RESULTS

Composition of the Catalysts in Examples 1 to 5:

The catalysts comprised 15.5% of Ag, 190 ppm of Li, 14 ppm of S, 200 ppm of W, 350 ppm of Cs, 310 ppm of Re and were, as indicated in the examples, calcined using different heating rates.

It was able to be shown that calcination at heating rates of at least 30 K/min has a positive effect on the selectivity and activity of the silver catalyst. Compared to catalysts calcined using lower heating rates, a selectivity improved by up to 2.6% and an activity improved by 7° C. could be detected. When the heating rate was too low, significant decreases in performance were apparent (Examples 4 and 5 (comparative examples)).

TABLE 2

Performance results for the catalysts examined

| | Heating rate [K/min] | Calcination gas | Selectivity [%] | Temperature [° C.] |
|---|---|---|---|---|
| Example 1 | 32 | N₂ (technical-grade, 6-8 ppm of O₂) | 90.9 | 242.4 |
| Example 2 | 40 | N₂ (technical-grade, 6-8 ppm of O₂) | 90.8 | 241.9 |
| Example 3 | 67 | N₂ (technical-grade, 6-8 ppm of O₂) | 91.2 | 244.0 |
| Example 4 (comparison) | 19 | N₂ (technical-grade, 6-8 ppm of O₂) | 88.6 | 251.0 |
| Example 5 (comparison) | 28 | N₂ (technical-grade, 6-8 ppm of O₂) | 89.8 | 241.7 |
| Example 6 (comparison) | 26 | lean air (6% by volume of O₂ in N₂) | 87.2 | 251.3 |

The invention claimed is:

1. A process for producing a catalyst for the oxidation of ethylene to ethylene oxide, which comprises
    a) impregnating a support comprising alumina with an aqueous solution comprising a silver-comprising compound and providing the impregnated support at a temperature $T_0$;
    b) heating the impregnated support from the temperature $T_0$ to a temperature $T_1$ at a heating rate in the range of 30 to 150 K/min.

2. The process according to claim 1, wherein the heating rate is in the range from 30 to 80 K/min.

3. The process according to claim 1, wherein the temperature $T_0$ is in the range from 5 to 20° C.

4. The process according to claim 1, wherein the temperature $T_1$ is in the range from 250 to 295° C.

5. The process according to claim 1, wherein the heating according to b) is effected by bringing the support into contact with an inert gas $I_1$, where $I_1$ comprises less than 10 ppm of oxygen.

6. The process according to claim 5, wherein $I_1$ has a temperature in the range from $T_1$ to $1.1\,T_1$.

7. The process according to claim 1, which further comprises c) maintaining the support which has been heated to the temperature $T_1$ at a temperature $T_2$ which is in the range from $0.90\, T_1$ to $1.1\, T_1$.

8. The process according to claim 7, wherein the support is maintained at the temperature $T_2$ according to c) by means of an inert gas $I_2$, where the inert gas $I_2$ comprises less than 10 ppm of oxygen and the inert gas has a temperature in the range from $T_2$ to $1.05\, T_2$.

9. The process according to claim 7, wherein the support is maintained at the temperature $T_2$ for a time in the range from 1 to 15 minutes, in c).

10. The process according to claim 1, which further comprises
d) cooling the support which has been maintained at a temperature $T_2$ to a temperature $T_3$ which is not more than 60° C.

11. The process according to claim 10, wherein the cooling according to d) is carried out in an atmosphere comprising at least 5% by volume, of oxygen.

12. The process according to claim 1, wherein the support comprising alumina is additionally impregnated with rhenium or with a rhenium-comprising compound, also additionally with tungsten or with a tungsten-comprising compound and/or with lithium or with a lithium-comprising compound and/or with cesium or with a cesium-comprising compound and the support is optionally impregnated with sulfur or with a sulfur-comprising compound in a).

13. The process according to claim 12, wherein the aqueous solution comprising a silver-comprising compound used in a) additionally comprises a rhenium-comprising compound, a tungsten-comprising compound and/or a lithium-comprising compound and/or a cesium-comprising compound, and optionally a sulfur-comprising compound.

14. The process according to claim 1, wherein the support comprising alumina which is provided according to a) has a cylindrical geometry, where the cylinder has a length in the range from 5 to 10 mm, an external diameter in the range from 5 to 10 mm and a ratio of external diameter in mm to wall thickness in mm in the range from 2.5 to 4.5.

15. A catalyst for the oxidation of ethylene to ethylene oxide obtainable or obtained by a process according to claim 1.

16. A process for preparing ethylene oxide by gas-phase oxidation of ethylene by means of molecular oxygen in a fixed-bed reactor in the presence of a catalyst according to claim 15.

17. The process according to claim 5, wherein the inert gas is nitrogen,
the heating rate is in the range from 40 to 75 K/min,
the temperature $T_0$ is in the range from 10 to 15° C.,
the temperature $T_1$ is in the range from 270 to 290° C. and
$I_1$ comprises from 5 to 9 ppm, of oxygen.

18. The process according to claim 7, wherein the support is maintained at the temperature $T_2$ according to c) by means of an nitrogen, where the nitrogen comprises from 5 to 9 ppm, of oxygen and the nitrogen has a temperature in the range from $T_2$ to $1.05\, T_2$ and the support is maintained at the temperature $T_2$ for a time in the range from 3 to 5 minutes, in c).

19. The process according to claim 10, wherein the cooling according to d) is carried out in an atmosphere comprising at least 15% by volume of air.

20. The process according to claim 12, wherein the aqueous solution comprising a silver-comprising compound used in a) additionally comprises a tungsten-comprising compound and/or a lithium-comprising compound and/or a cesium-comprising compound, and optionally a sulfur-comprising compound.

21. The process according to claim 1, wherein the heating according to b) is effected by bringing the support into contact with an inert gas $I_1$, wherein the inert gas is nitrogen and said $I_1$ comprises less than 10 ppm of oxygen.

22. The process according to claim 7, wherein the support is maintained at the temperature $T_2$ according to c) by means of an inert gas $I_2$, where the inert gas $I_2$ comprises from 5 to 9 ppm, of oxygen and the inert gas has a temperature in the range from $T_2$ to $1.05\, T_2$.

* * * * *